United States Patent [19]

Cheever et al.

[11] Patent Number: 5,320,947
[45] Date of Patent: Jun. 14, 1994

[54] IMMUNE REACTIVITY TO EXPRESSED ACTIVATED ONCOGENES FOR DIAGNOSIS OF MALIGNANCY

[75] Inventors: Martin A. Cheever, Mercer Island; David J. Peace, Seattle, both of Wash.

[73] Assignee: Washington Research Foundation, Seattle, Wash.

[21] Appl. No.: 820,409

[22] Filed: Jan. 13, 1992

Related U.S. Application Data

[63] Continuation-in-part of Ser. No. 470,645, Jan. 26, 1990, abandoned.

[51] Int. Cl.$^5$ .......................... C07K 3/00; C12Q 1/00; C12N 5/00; A01N 63/00
[52] U.S. Cl. .................................... 435/29; 435/7.1; 435/7.23; 435/240.1; 435/240.2; 424/520; 530/351; 530/395
[58] Field of Search .............. 435/6, 7.1, 172.2, 240.1, 435/240.2, 29, 7.23; 530/351, 395; 424/93, 520

[56] References Cited

U.S. PATENT DOCUMENTS

| | | | |
|---|---|---|---|
| 4,376,110 | 3/1983 | David et al. | 436/513 |
| 4,411,990 | 10/1983 | Salmon et al. | 435/32 |
| 4,643,968 | 2/1987 | Weaver | 435/32 |
| 4,820,631 | 4/1989 | Lacal et al. | 435/6 |
| 4,861,589 | 8/1989 | Ju et al. | 424/93 |

OTHER PUBLICATIONS

A. Balmain, "Transforming ras oncogenes and multistage carcinogenesis," *Br. J. Cancer*, 51:1-7, 1985.
Allan Balmain et al., "An Approach to the Molecular Mechanisms of Cancer Induction," *Journal of Pathology* 149:3-8, 1986.
A. Bloch, "Growth and differentiation signals as determinants of cancer cell proliferation," *Chem. Abs.* 111(21):192290z, 1989.
Walter Bodmer, "T-cell immune response to cancer—a new look," *Hum. Immunol.* 30(4):259-261, 1991.
Johannes L. Bos et al., "Prevalence of ras gene mutations in human colorectal cancers," *Nature* 327:293-297, 1987.
Johannes L. Bos, "The ras gene family and human carcinogenesis," *Mutation Research* 195:255-271, 1988.
Johannes L. Bos, "ras Oncogenes in Human Cancer: A Review," *Cancer Research* 49:4682-3689, 1989.
Joseph P. Brown et al., "Protein Antigens of Normal and Malignant Human Cells Identified by Immunoprecipitation with Monoclonal Antibodies," *J. Biol. Chem.* 255(11):4980-4983, 1980.
Walter Carney, "Human tumor antigens and specific tumor therapy," 363-364, 1988. The Symposium was held in Keystone, Colorado on Apr. 23-30, 1988.
Walter P. Carney et al., "Monoclonal Antibodies for Detecting Oncogenic ras Proteins in Cancer Cells," *Clin. Chem.* 34:1698-1699, 1988.
Pierre Chardin, "The ras superfamily proteins," *Biochimie* 70:865-868, 1988.
"Clinical Laboratory Methods for Detection of Cellular Immune Function," (eds.), Stites, Stobo and Wells, *Basic and Clinical Immunology* (Sixth edition) Appleton & Lange, 1987, pp. 295-298.

(List continued on next page.)

Primary Examiner—Robert J. Hill, Jr.
Assistant Examiner—Gian Wang
Attorney, Agent, or Firm—Seed and Berry

[57] ABSTRACT

Methods for the detection, monitoring and treatment of malignancies are disclosed. Detection of the proliferation of T cells in response to in vitro exposure to a protein expression product of an activated oncogene or cancer-related gene associated with a malignancy, or detection of immunocomplexes formed between the protein expression product and antibodies in body fluid, allows the diagnosis of the presence of a malignancy. The present invention also discloses methods and compositions for treating a malignancy.

2 Claims, 6 Drawing Sheets

OTHER PUBLICATIONS

E. N. Dotsika and C. J. Sanderson, "A fluorometric assay for determining cell growth in lymphocyte proliferation and lymphokine assays," *Chem. Abs.* 108(5):35974w, 1988.

J. A. Debrin et al., "Preliminary Evidence of an Association Between an Activated Cellular Transforming Gene and a Tumor-Specific Transplantation Antigen," *UCLA Symposium of Molec. & Cell Biology* 24:223-225, 1982.

James R. Feramisco et al., "Microinjection of the Oncogene Form of the Human H-ras (T-24) Protein Results in Rapid Proliferation of Quiescent Cells," *Cell* 38:;109-117, 1984.

Kathleen Forrester et al., "Detection of high incidence of K-ras oncogenes during human colon tumorigenesis," *Nature* 327:298-303, 1987.

G. B. Gehly et al., "Chimeric BCR-abl Messenger RNA as a Marker for Minmal Residual Disease in Patients Transplanted for Philadelphia Chromosome-Positive Acute Lymphoblastic Leukemia," *Blood* 78:458-465, 1991.

P. Horan Hand et al., "Monoclonal antibodies of predefined speficity detect activated ras gene expression in human mammary and colon carcinomas," *Proc. Natl. Acad. Sci. USA* 81:5227-5231, 1984.

Brian E. Huber, "Therapeutic opportunities involving cellular oncogenes: novel approaches fostered by biotechnology," *FASEB J.* 3:5-13, 1989.

Jean L. Marx, "Gene Signals Relapse of Breast, Ovarian Cancers," *Science* 244:654-655, 1989.

Jami McLaughlin et al., "In vitro transformation of immature hematopoietic cells by the P210 BCR/ABL oncogene product of the Philadelphia chromosome," *Proc. Natl. Acad. Sci. USA* 84:6558-6562, 1987.

Jami McLaughlin et al., "Alternative Forms of the BCR-ABL Oncogene Have Quantitatively Different Potencies for Stimulation of Immature Lymphoid Cells," *Mol. & Cell. Biol.* 9:1866-1874, 1989.

Janice M. Nigro et al., "Mutations in the p53 gene occur in diverse human tumour types," *Nature* 342:705-707, 1989.

Henry L. Niman et al., "Anti-peptide antibodies detect oncogene-related proteins in urine," *Proc. Natl. Acad. Sci. USA* 82:7924-7928, 1985.

E. W. Raines and R. Ross, "Platelet-derived Growth Factor," *J. Biol. Chem.* 257(9):5154-5160, 1982.

E. P. Reddy et al., "A point mutation is responsible for the acquisition of transforming properties by the T24 human bladder carcinoma oncogene," *Nature* 300:149-152, 1982.

Eugenio Santos and Angle R. Nebreda, "Structural and functional properties of ras proteins," *Faseb J.* 3:2151-2163, 1989.

Thomas Y. Shih and Maureen O. Weeks, "Oncogenes and Cancer: The p21 ras genes," *Cancer investigation* 2(2):109-123, 1984.

Dennis J. Slamon et al., "Studies of the HER-2/neu Proto-oncogene in Human Breast and Ovarian Cancer," *Science* 244:707-712, 1989.

Dennis W. Stacey and Hsiang-Fu Kung, "Transformation of NIH 3T3 cells by microinjection of Ha-ras p21 protein," *Nature* 310:508-511, 1984.

A. Thor et al., "Monoclonal antibodies define differential ras gene expression in malignant and benign colonic diseases," *Nature* 311:302-303, 1984.

David B. Weiner et al., "A point mutation in the neu oncogene mimics ligand induction of receptor aggregation," *Nature* 339:230-231, 1989.

David W. Yandell et al., "Oncogenic Point Mutations in the Human Retinoblastoma Gene: Their Application to Genetic Counseling," *N. Engl. J. Med.* 321:1689-1695, 1989.

IMMUNE REACTIVITY TO EXPRESSED ACTIVATED ONCOGENES FOR DIAGNOSIS OF MALIGNANCY

CROSS REFERENCE TO RELATED APPLICATION

This application is a continuation-in-part to Ser. No. 07/470,645, filed Jan. 26, 1990, now abandoned, which is incorporated herein by reference.

TECHNICAL FIELD

The present invention is generally directed toward the detection, monitoring, and treatment of malignancies through the use of a cancer patient's own immune reactivity to the protein expression product of an activated oncogene or cancer-related gene associated with malignancy.

BACKGROUND OF THE INVENTION

Despite enormous investments of financial and human resources, cancer remains one of the major causes of death. A common characteristic of malignancies is uncontrolled cell growth. Cancer cells appear to have undergone a process of transformation from the normal phenotype to a malignant phenotype capable of autonomous growth. Mutation of somatic cell genes is considered to be a common primary event that results in the transformation of normal cells to malignant cells. The malignant phenotypic characteristics encoded by the mutated genes are passed on during cell division to the progeny of the transformed cells. Various genes involved with transformation have been designated as oncogenes. Oncogenes were originally identified as components of the genetic material of oncogenic viruses. The homologous genes on human chromosomes are commonly termed oncogenes or proto-oncogenes.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene).

Proto-oncogenes are believed to be essential for certain aspects of normal cellular physiology. Certain proto-oncogenes appear to be activated to a cellular oncogene through quantitative mechanisms that result from increased or deregulated expression of an essentially normal gene product. For example, the myc gene family has been associated with initiation and/or progression of certain human lymphomas and carcinomas, whose transforming activation is the result of quantitative mechanisms. Alternatively, other proto-oncogenes appear to be activated to transforming cellular oncogenes through qualitative mechanisms, including mutation in the coding sequence of the gene. This creates a gene product with an altered primary structure and biochemical properties as a result of one or more differences in the amino acid sequence of the protein. For example, the ras gene family, causally associated with the most common forms of human malignancy (e.g., colon cancer) is activated as a result of single codon changes.

Studies to develop cancer therapies have, in general, focused on the use of characteristic differences between normal and malignant cells. Mutated, translocated or otherwise overexpressed proto-oncogenes and the products of such genes represent potential identifiable characteristic differences between normal and malignant cells. The identified differences have been utilized in attempts to develop diagnostic assays or therapeutic regimens.

An approach to developing a diagnostic assay has been to attempt to quantify the expressed product of an oncogene in tissue or body fluids, utilizing antibodies directed toward the unique or abnormal oncogene product. In general, xenogeneic antibodies have been raised against the abnormally expressed proto-oncogene product. Problems in the development of diagnostic assays based on detecting abnormal oncogene products include the following factors: (1) a lack of antibodies with high specificity, affinity and selectivity for the abnormal product; (2) only small amounts of abnormal oncogene product may be released by tumor cells; (3) oncogenic products may be released only intermittently by tumor cells; (4) the oncogene product may be absorbed out of the body fluid by antibody or may be formed into immune complexes; and (5) the free antigen may be rapidly cleared or degraded.

Due to the difficulties in the current approaches to cancer diagnosis and therapy, there is a need in the art for improved methods and compositions. The present invention fills this need, and further provides other related advantages.

SUMMARY OF THE INVENTION

Briefly stated, the present invention provides a variety of methods for the detection of a malignancy in a warm-blooded animal, wherein an activated oncogene or cancer-related gene is associated with the malignancy. The methods may be used on a one time basis when a malignancy is suspected or on a periodic basis to monitor an individual with an elevated risk of acquiring a malignancy. In one embodiment, the method comprises the steps of: (a) isolating T cells from a warm-blooded animal; (b) incubating the T cells with at least one protein expression product of an activated oncogene or cancer-related gene associated with the malignancy; and (c) detecting the presence or absence of proliferation of the T cells, thereby determining the presence or absence of the malignancy. In another embodiment, the method comprises the steps of: (a) contacting a body fluid, suspected of containing antibodies specific for a protein expression product of an activated oncogene or cancer-related gene associated with the malignancy, with at least one protein expression product of an activated oncogene or cancer-related gene associated with the malignancy; (b) incubating the body fluid under conditions and for a time sufficient to allow immunocomplexes to form; and (c) detecting the presence or absence of one or more immunocomplexes formed between the protein expression product and antibodies in the body fluid specific for the protein expression product, thereby determining the presence or absence of the malignancy.

In another aspect, the present invention provides methods for monitoring the effectiveness of cancer therapy in a warm-blooded animal with a malignancy, wherein an activated oncogene or cancer-related gene is associated with the malignancy. In one embodiment, the method comprises the steps of: (a) contacting a first body fluid sample, taken from the warm-blooded animal prior to initiation of therapy, with at least one protein expression product of an activated oncogene or cancer-related gene associated with the malignancy; (b) incubating the body fluid under conditions and for a time sufficient to allow immunocomplexes to form; (c) detecting immunocomplexes formed between the protein expression product and antibodies in the body fluid specific for the protein expression product; (d) repeating steps (a), (b), and (c) on a second body fluid sample taken from the animal subsequent to the initiation of therapy; and (e) comparing the number of immunocomplexes detected in the first and second body fluid samples, thereby monitoring the effectiveness of the therapy in the animal.

The present invention is also directed toward methods for treating a malignancy in a warm-blooded animal, wherein an activated oncogene or cancer-related gene is associated with the malignancy. In one embodiment, the method comprises the steps of: (a) isolating T cells from a warm-blooded animal; (b) incubating the T cells in the presence of at least one protein expression product of an activated oncogene or cancer-related gene associated with the malignancy, such that the T cells proliferate; and (c) administering to the warm-blooded animal an effective amount of the proliferated T cells. In another embodiment, the method comprises the steps of: (a) isolating T cells from a warm-blooded animal; (b) incubating the T cells in the presence of at least one protein expression product of an activated oncogene or cancer-related gene associated with the malignancy, such that the T cells proliferate; (c) cloning one or more cells that proliferated in the presence of the protein expression product; and (d) administering to the warm-blooded animal an effective amount of the cloned T cells. In a third embodiment, the method comprises immunizing the animal with at least one protein expression product of an activated oncogene or cancer-related gene associated with the malignancy.

Within a related aspect, the present invention provides anti-cancer therapeutic compositions comprising T cells proliferated in the presence of at least one protein expression product of an activated oncogene or cancer-related gene associated with a malignancy, in combination with a physiologically acceptable carrier or diluent.

These and other aspects of the present invention will become evident upon reference to the following detailed description and attached drawings.

DETAILED DESCRIPTION OF THE INVENTION

Figure 1:
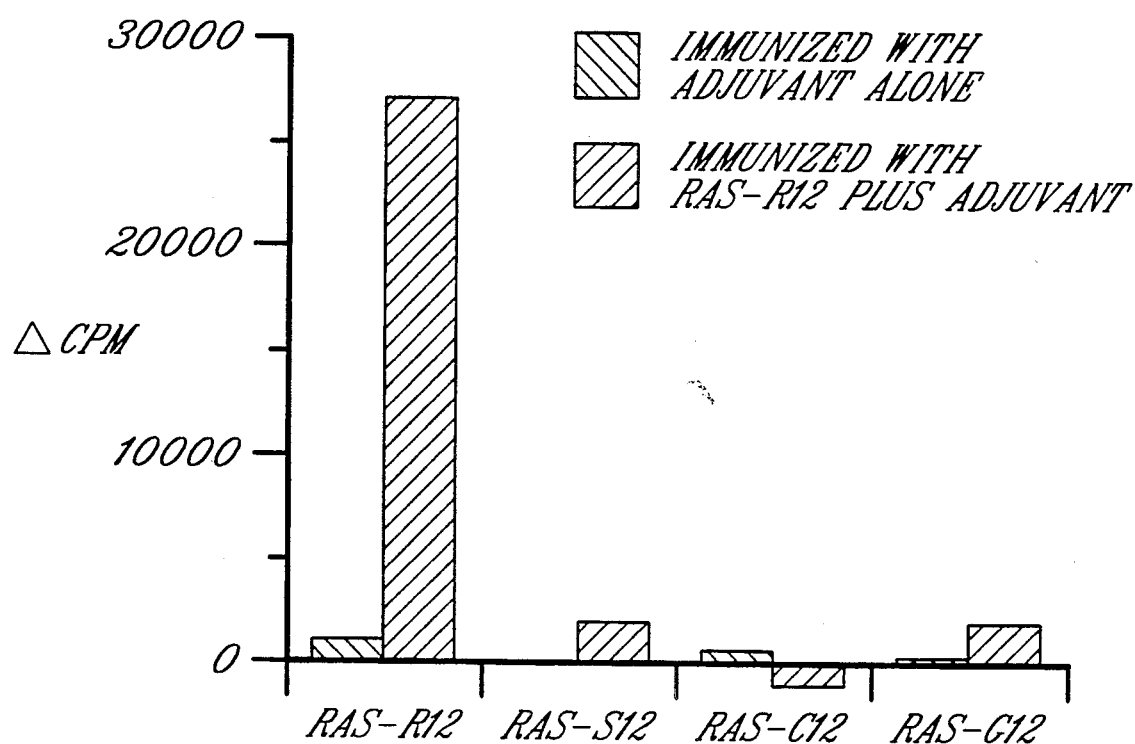
FIG. 1 graphically illustrates that specific T cell responses to point-mutated ras peptide can be generated by in vivo priming on day 0 with 50 μg of a peptide of 12 amino acid length constructed identically to murine ras-p21 (amino acids 5–16) but with the substitution of arginine for the glycine normally found at position 12 (i.e., position 12 of ras-p21 but position 8 of the peptide). This peptide is denoted as ras p5–16[R12] or as ras-R12. Mice were immunized with ras-R12 peptide plus adjuvant or with adjuvant alone. After 10 days, the draining lymph nodes were harvested and lymphocytes stimulated in vitro with ras-R12 peptide or as specificity controls with similar peptides substituted with serine, cysteine or glycine at position 12 as opposed to arginine, denoted as ras-S12, ras-C12 and ras-G12, respectively. Four days later, cultures were pulsed with [$^3$H]-thymidine (3HTdR) for 8 hours, as described in Example 1 below. Results are represented as ΔCPM.

Prior to setting forth the invention, it may be helpful to an understanding thereof to set forth definitions of certain terms to be used hereinafter.

Activated oncogene - as used herein, refers to proto-oncogenes that have become activated, leading to the expression of protein products with amino acid sequences other than those of the protein products expressed by the normal proto-oncogenes.

Cancer-related gene - as used herein, refers to any altered gene (other than an oncogene) associated with the development or maintenance of the malignant phenotype. Examples of such altered genes include mutants of the p53 tumor suppressor gene.

Protein expression product - as used herein, includes proteins, polypeptides, and peptides; and may be an intact molecule, a fragment thereof, or a functional equivalent thereof; and may be genetically engineered.

Proliferation of T cells - as used herein, includes the multiplication of T cells as well as the stimulation of T cells leading to multiplication, i.e., the initiation of events leading to mitosis and mitosis itself. Methods for detecting proliferation of T cells are discussed below.

As noted above, the present invention is directed toward methods and compositions for the diagnosis, monitoring and treatment of malignancies in a warm-blooded animal, wherein activated oncogenes or cancer-related genes are associated with the malignancies. The disclosure of the present invention shows that the protein expression products of activated oncogenes and cancer-related genes can be recognized by thymus-dependent lymphocytes (hereinafter "T cells") and, therefore, the autochthonous immune response can be utilized to diagnose and treat malignancies expressing such protein expression products.

Activation of proto-oncogenes is associated with or leads to transformation and expression of the malignant phenotype. Activation by mechanisms such as mutation or chromosomal translocation (gene rearrangement) creates a gene product with altered primary structure, i.e., a protein expression product with one or more amino acid differences relative to the normal protein expressed by the proto-oncogene. Mutation mechanisms include point mutation of nucleotides, recombination, deletion and insertion. Examples of activation of proto-oncogenes through mutation include activation of ras and neu proto-oncogenes. Chromosomal translocation results in a fused protein, such as that associated with chronic myeologenous leukemia. Similarly, cancer-related genes express abnormal protein products with altered amino acid sequences. For example, mutation of the p53 tumor suppressor gene results in amino acid substitutions.

As disclosed within the present invention, protein products with altered primary structure expressed by activated oncogenes and cancer-related genes are recognized by T cells. Such abnormal protein expression products "turn over" within cells, i.e., undergo a cycle wherein a protein is synthesized, functions and then is degraded and replaced by a newly synthesized molecule. The ensuing peptide fragments from the degraded protein bind to major histocompatibility complex (MHC) antigens. By display of an abnormal peptide bound to MHC antigen on the cell surface and recognition by host T cells of the combination of abnormal peptide plus self MHC antigen, a malignant cell will be immunogenic to T cells. The exquisite specificity of the T cell receptor enables individual T cells to discriminate between fragments of proteins which differ by a single amino acid residue.

During the immune response to an abnormal peptide, T cells expressing a T cell receptor with high affinity binding of the peptide-MHC complex will bind to the peptide-MHC complex and thereby become activated and induced to proliferate. In the first encounter with an abnormal peptide, small numbers of immune T cells will proliferate and differentiate into effector and memory T cells. The primary immune response will occur in vivo but is not detected in vitro. Subsequent encounter with the same antigen by the memory T cell will lead to a faster and more intense immune response. The secondary response will occur either in vivo or in vitro. The in vitro response is easily gauged by measuring the degree of proliferation of the T cell population re-exposed in the antigen. Proliferation of the T cell population in response to a particular antigen is considered to be indicative of prior exposure or priming to the antigen.

Within one aspect of the present invention, a malignancy in which an activated oncogene or cancer-related gene is associated with the malignancy may be detected. An immune response to an abnormal protein expressed by an activated oncogene or cancer-related gene, once generated, can be long-lived and can be detected long after immunization, regardless of whether the protein is present or absent in the body at the time of testing. In one embodiment, prior exposure of a warm-blooded animal, such as humans, to the protein expression product of an activated oncogene or cancer-related gene can be detected by examining for the presence or absence of T cell proliferative responses. More specifically, T cells isolated from an individual by routine techniques are incubated with a protein expression product of an activated oncogene or cancer-related gene. Examples of oncogenes include ras, src, abl, fgr, rel, yes, fes, net, mos, raf, erb B, erb A, fms, neu, ros, kit, sea, sis, myc, myb, fos, ski, jun and ets. Alternatively, more than one protein expression product can be examined with the T cell sample. It may be desirable to incubate individual aliquots of a T cell sample with only one protein expression product if such a protein interferes with another protein expression product.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium.

A representative example of an activated oncogene that expresses a protein product capable of immunizing T cells is the ras oncogene. Ras proto-oncogenes encode a highly conserved family of 21Kd proteins (189 amino acids in length) collectively designated as "p21". p21 proteins bind to the inner aspect of the cell membrane, associate with guanosine nucleotides and have intrinsic GTPase activity. p21 proteins have been implicated as important intermediary signalling proteins which regulate cell growth and differentiation. Ras oncogenes were first detected as genetic material in the transforming Harvey and Kirsten murine sarcoma retroviruses. In animals, carcinogens induce very specific and predictable mutations, usually involving codons 12, 13, 59 and/or 61, which impair the intrinsic GTPase activity of the p21 molecule and confer transforming activity. The human genome contains at least three ras proto-oncogene homologs of the viral ras oncogene, denoted as K-ras, H-ras and N-ras which are located on three separate human chromosomes. Each of the three ras genes can become activated through specific mutation. Mutations of one of the three ras proto-oncogenes occurs commonly in a variety of human malignancies including pancreas adenocarcinoma, thyroid follicular carcinoma, colon adenocarcinoma, seminoma, lung adenocarcinoma, liver adenocarcinoma, melanoma, myeloid leukemia, and myeloma. The disclosure of the present invention shows that once mutated, the expressed protein product of any of the three ras genes by virtue of a single amino acid substitution may be recognized by autochthonous T cells.

Figure 3:
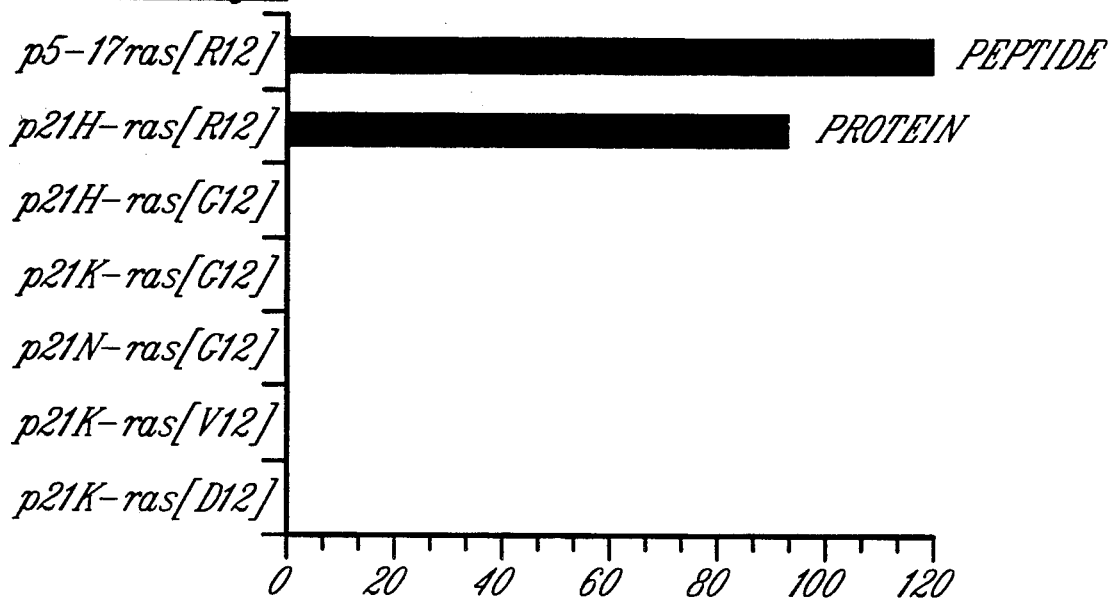
FIG. 3 graphically illustrates that T cells specific for a ras peptide respond specifically to intact ras p21 protein containing the same residue substitution. This peptide, denoted as p5–17[R12], consists of 13 amino acid residues and was constructed identically to murine ras-p21 (amino acids 5–17) but with the substitution of arginine (R) for the glycine (G) normally found at position 12 of ras-p21. Cloned B6 T cells specific for the Arg-12 ras peptide were cultured with irradiated B6 spleen cells and either p5–17[R12] or intact ras p21 proteins bearing the designated amino acid at position-12 (1 μg/ml). Proliferative responses were measured after four days (as described in FIG. 1). The data represent the mean of triplicate determinations of the c.p.m. of incorporated 3HTdR. The standard deviations were <10% of the c.p.m.

For example, within the present invention, peptides consisting of 12 or 13 amino acid residues which corresponded to the amino acid sequence from residues 5–16, 5–17, or 4–16 of p21 were constructed to contain either the normal glycine (termed Gly-12 or G-12), or arginine (termed Arg-12 or R-12), or serine (termed Ser-12 or S-12), or cysteine (termed Cys-12, or C-12). C57BL/6 mice were immunized with a single dose of the Arg-12 peptide. Lymphocytes from immunized mice were subsequently tested for proliferative response to the above peptides in vitro and, as shown in FIG. 1, were found to proliferate specifically in response to the Arg-12 peptide, but not the Gly-12, Cys-12, or Ser-12 peptides. In addition, the lymphocytes from mice immunized with the Arg-12 peptide were shown (FIG. 3) to proliferate specifically in response to stimulation by the intact p21 protein containing this same amino acid substitution (Oncogene Science, Inc., Manhasset, N.Y.).

Figure 4:
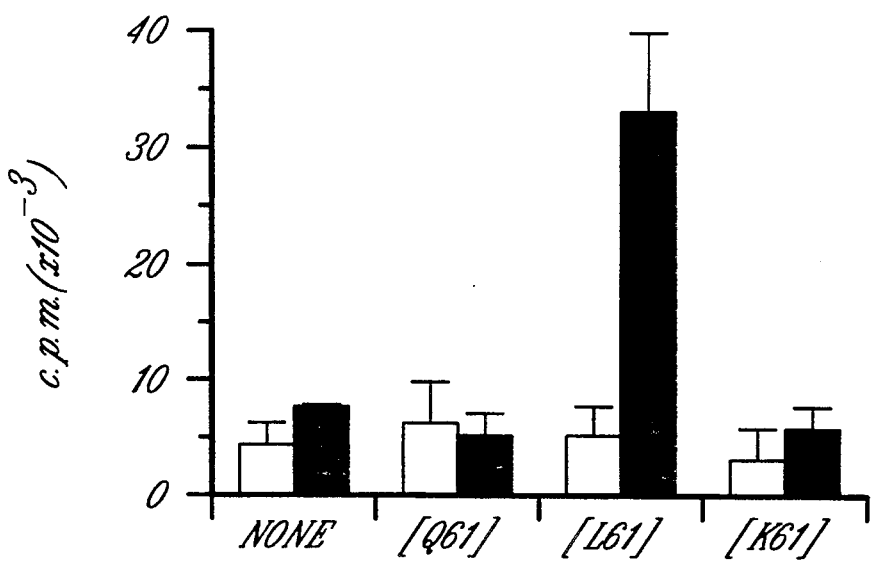
FIG. 4 shows that specific T cell responses can be generated by in vivo priming with a peptide of 13 amino acid length constructed identically to murine ras-p21 (amino acids 54–66) but with the substitution of leucine (L) for the glutamine (Q) normally found at position 61 of ras-p21. This peptide is denoted as p54–66[L61] or [L61]. C3H/HeN mice were immunized twice subcutaneously at two week intervals with Ribi adjuvant alone or adjuvant emulsified with p54–66[L61] ras peptide (100 μg). Two weeks after the final immunization, spleen cells from mice injected with adjuvant alone (open bar) or adjuvant plus p54–66[L61] ras peptide (black bar) were harvested and tested in vitro for proliferative response to the indicated p54–66 ras peptide (100 μg/ml). The peptide containing the substitution of lysine (K) for glutamine at position 61 is denoted as [K61]. The data represent the mean of triplicate determinations of the c.p.m. of incorporated $^3$HTdR±S.D.
Figure 5A:
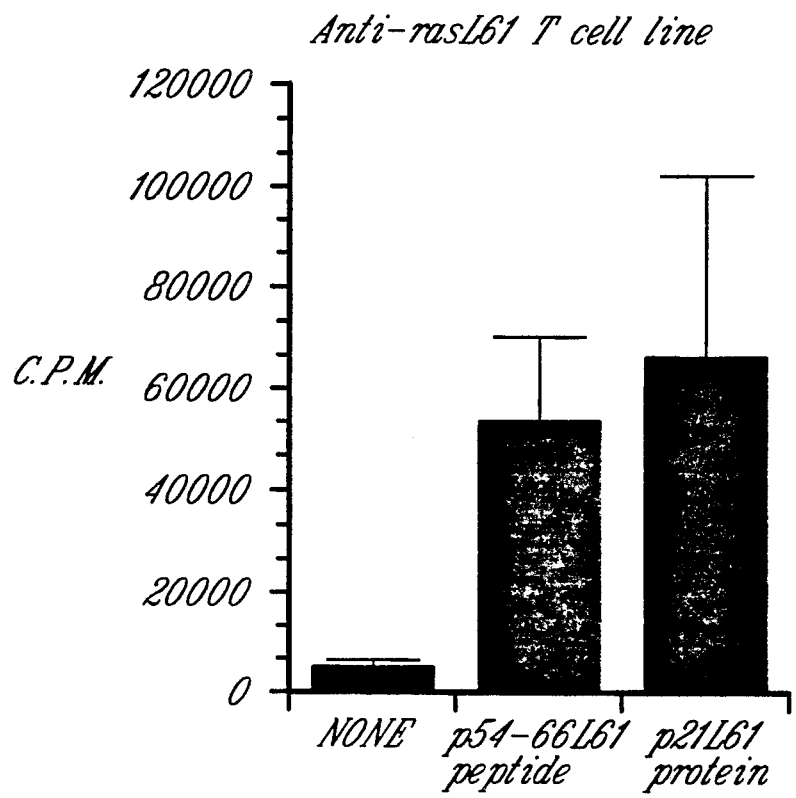
FIGS 5A-B graphically illustrates that intact ras p21[L61] protein is specifically recognized by a ras peptide-induced T cell line. Specific T cell lines and clones were generated and maintained as described in Example 2 below. A T cell line which exhibits specific reactivity to the ras peptide p54–66[L61] (FIG. 5A) and a T cell clone which exhibits specific reactivity to the ras peptide p5–17[R12] (FIG. 5B) were stimulated with (a) no antigen, (b) sensitizing ras peptide, or (c) intact ras p21[L61] protein. The ras p54–66[L61] specific T cell line was of C3H origin and the ras p5–17[R12] specific T cell clone was of B6 origin. Proliferative assays were performed with syngeneic irradiated spleen cells as antigen presenting cells (as described in FIG. 1). Stimulating peptides and proteins were used at a concentration of 5 μg/ml. The ras p21[L61] protein was produced in E. coli HB101 using the prokaryotic expression plasmid pHR-L9 and purified by sequential DEAE-Sephacel and Sephadex column chromatography. The data represent the mean c.p.m. of incorporated $^3$HTdR±S.D.
Figure 5B:
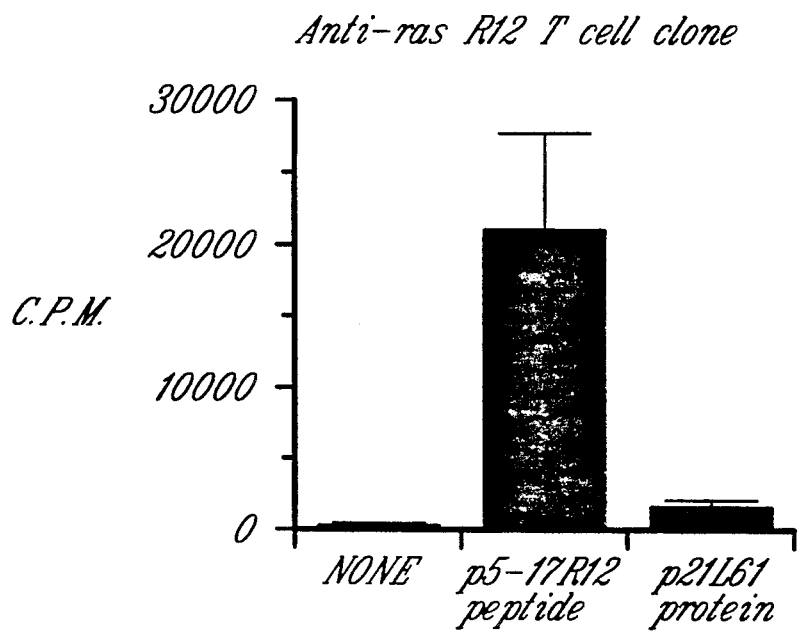
Figure 6A:
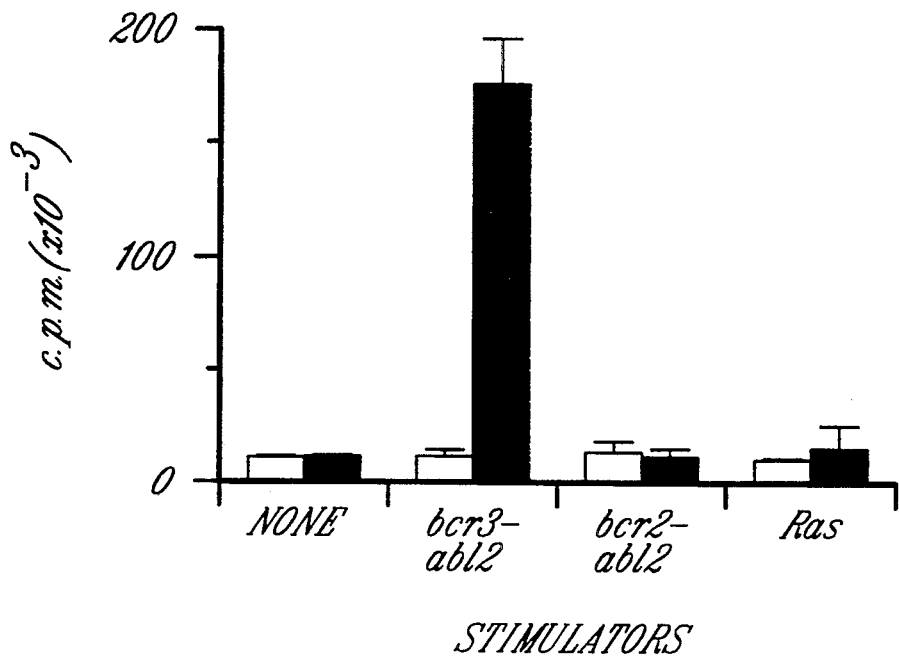
FIGS. 6A-B graphically illustrate that lymphocytes from spleens and lymph nodes of BALB/c mice primed in vivo with bcr3-abl2 12-amino acid peptide corresponding to the joining region of p210$^{bcr-abl}$ chimeric protein proliferate specifically in response to the sensitizing peptide in vitro. Ten days following immunization with peptide, draining lymph node cells (FIG. 6A) and spleen cells (FIG. 6B) were cultured alone or with bcr3-abl2 12 mer peptide, or bcr2-abl2 12 mer peptide, or ras-c12 12 mer peptide at 25 µg/ml, and assayed after 96 hours for proliferation by [$^3$H] thymidine uptake. The data represent the mean of triplicate determinations of the c.p.m.+S.D.
Figure 6B:
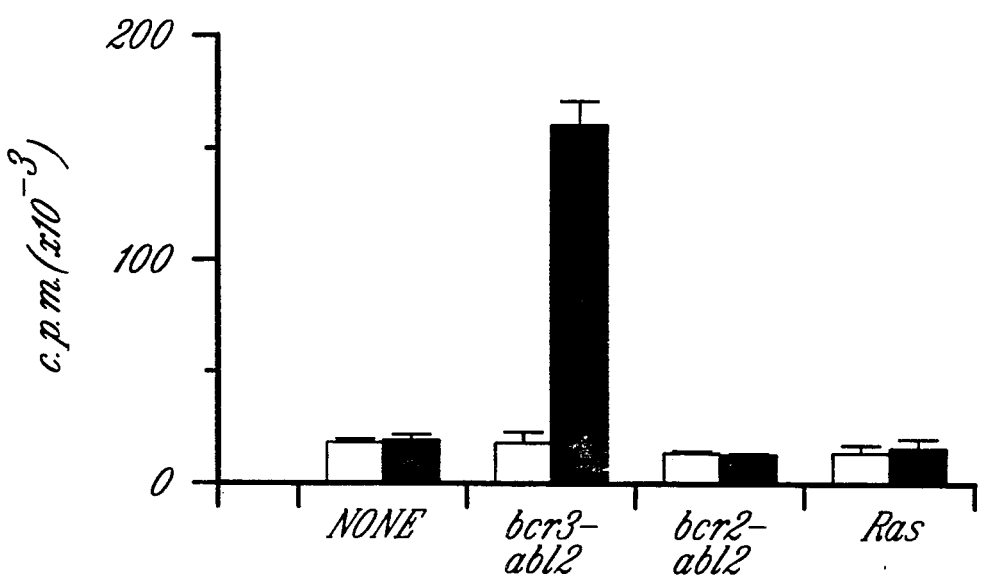

Another example of a peptide suitable within the present invention is ras p54–66[L61]. This peptide consists of 13 amino acid residues which correspond to the amino acid sequence from residues 54–66 of p21, except leucine (L) has been substituted for the glutamine (Q) normally found at position 61. Lymphocytes from mice immunized with p54–66[L61] were found to proliferate in vitro, as shown in FIG. 4, specifically in response to the Leu-61 peptide, but not to Gln-61 or Lys-61 peptides. In addition, the lymphocytes from mice immunized with the Leu-61 peptide were shown (FIG. 5A) to proliferate specifically in response to stimulation by the intact p21 protein containing the same amino acid substitution.

Another representative example of an activated oncogene that expresses a protein product capable of immunizing T cells is the fusion bcr-abl oncogene. The hallmark of chronic myelogenous leukemia (CML) is the translocation of the c-abl oncogene from chromosome 9 to the specific breakpoint cluster region (bcr) of the BCR gene on chromosome 22. The t(9;22) (q34; q11) translocation is exceedingly consistent and present in more than 95% of patients with CML. The translocation of the c-abl proto-oncogene on chromosome 9 to the breakpoint cluster region (bcr) on chromosome 22 forms a new fusion gene, termed bcr-abl, which encodes a 210 kD chimeric protein with abnormal tyrosine kinase activity. In humans, the bcr-abl protein is expressed only by leukemia cells. $p210^{bcr-abl}$ can stimulate the growth of hematopoietic progenitor cells and is essential for the pathogenesis of CML. In CML, the bcr breakpoint is generally between exons 2 and 3 or exons 3 and 4. Depending on the location of the breakpoint within the bcr gene, the mRNA either includes or excludes bcr exon 3. Regardless of the location of the breakpoint, the bcr-abl reading frames are fused in frame and the translocated mRNA encodes a functional 210 kD chimeric protein consisting of 1,004 c-abl encoded amino acids plus either 902 or 927 bcr encoded amino acids—both of which are enzymatically active as protein kinases. In acute lymphoblastic leukemia (ALL), c-abl is translocated to chromosome 22 but to a different region of the bcr gene, denoted BCRI, which results in the expression of a $p185-190^{bcr-abl}$ chimeric protein kinase. $p185-190^{bcr-abl}$ is expressed in approximately 10% of children and 25% of adults with ALL.

The disclosure of the present invention shows that the joining region of the bcr-abl protein is immunogenic to T cells. Immunization of mice with synthetic peptides corresponding to the joining region elicited peptide-specific CD4+ class II-MHC-restricted T cells. For example, an immunizing peptide was composed of 6 bcr, 1 fusion, and 5 c-abl amino acids. The bcr-abl peptide-specific T cells recognized only the combined sequence of bcr-abl amino acids and not bcr or c-abl amino acid sequences alone. Thus, immunity was directed specifically against the 12 amino acid residues of the joining region. Importantly, p210$^{bcr-abl}$ protein effectively stimulated the bcr-abl peptide-specific T cells. Therefore, p210$^{bcr-abl}$ protein can be processed by antigen-presenting cells so that the joining region segment is bound to class II MHC molecules in a configuration similar to that of the immunizing peptide and in a concentration high enough to stimulate the antigen-specific T cell receptor.

Similarly, proteins (or peptides based upon or derived therefrom) other than p21 and bcr-abl may be isolated or constructed by a variety of known techniques. It will be appreciated by those skilled in the art that it may be desirable to increase the length of an overall peptide or of the native flanking regions to facilitate the induction of T cell responses. As discussed above, protein expression products of activated oncogenes other than ras, or cancer-related genes (i.e., with an amino acid sequence different from that of the proteins expressed by normal proto-oncogenes or normal genes) are suitable for use within the methods described herein.

Figure 2:
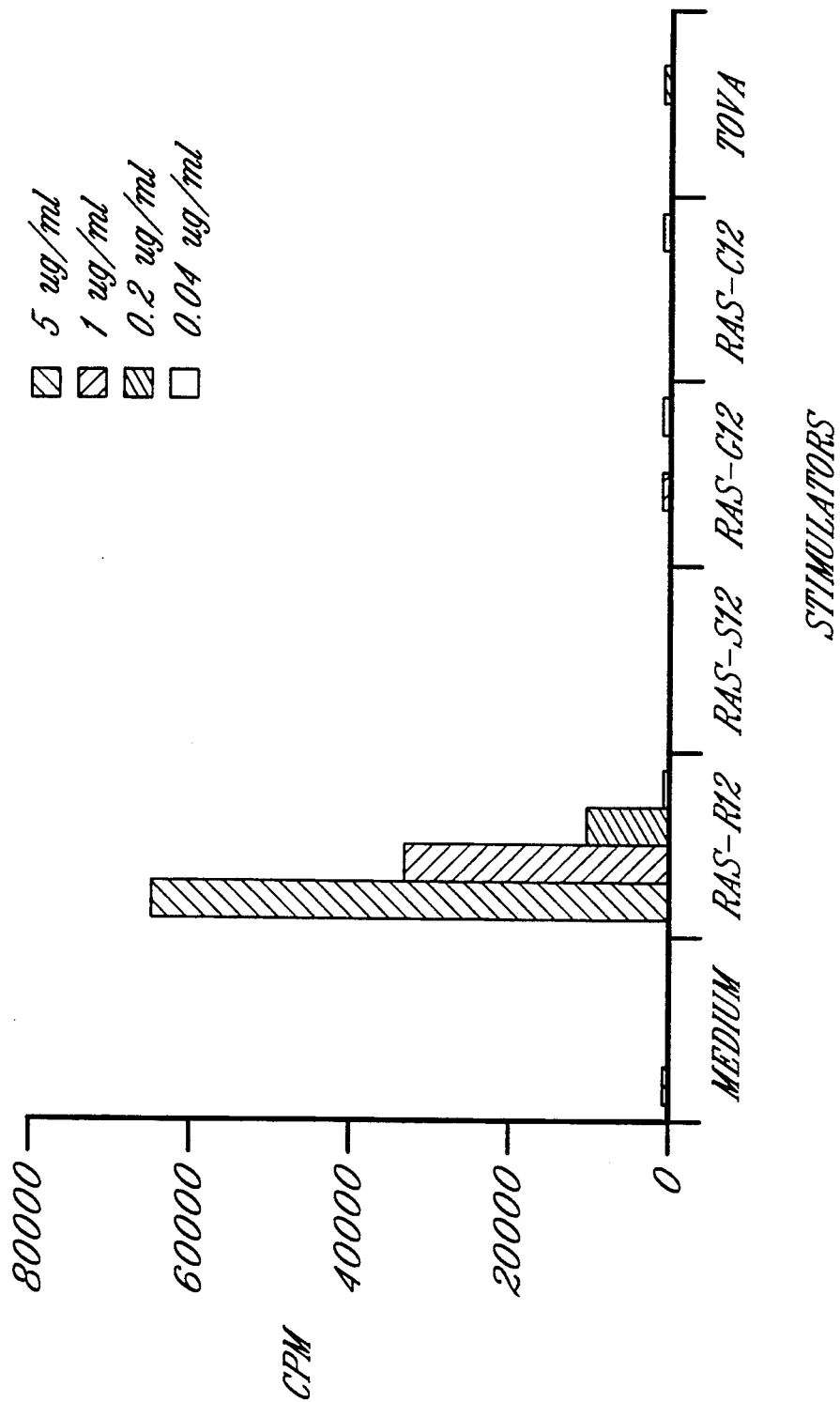
FIG. 2 shows that ras-peptide specific T cells grown long-term in vitro in response to intermittent stimulation by ras-peptide retain specific function. T cells derived from mesenteric lymph nodes of C57BL/6 mice primed to ras-R12 (as defined for FIG. 1 above) were cultured long-term in vitro in response to intermittent stimulation with ras-R12 peptide (5 μg/ml) on irradiated B6 spleen cells (3000 rad) as antigen presenting cells. The specificity of the T cell line was tested on day 85 by stimulating with graded concentrations of various ras peptides (as defined for FIG. 1 above) or with trypsinized OVA (TOVA) containing several potential immunogenic peptides. Data is represented as $^3$HTdR uptake in counts per minute (c.p.m.).

For therapeutic purposes, T cells that proliferate in the presence of one or more protein expression products of activated oncogenes or cancer-related genes can be expanded in number either in vitro or in vivo. Proliferation of such T cells in vitro may be accomplished in a variety of ways. For example, the T cells can be re-exposed to one or more protein expression products. It may be desirable to repeat the exposure of T cells to the protein to induce proliferation. As shown in FIG. 2, protein expression product-specific T cells can be grown to large numbers in vitro with retention of specificity in response to intermittent restimulation with the immunizing peptide.

Alternatively, one or more T cells that proliferate in the presence of a protein expression can be expanded in number by cloning. Methods for cloning cells are well known in the art. For example, T cell lines may be established in vitro and cloned by limiting dilution. Responder T cells are purified from the peripheral blood of sensitized patients by density gradient centrifugation and sheep red cell rosetting and established in culture by stimulating with the nominal antigen in the presence of irradiated autologous filler cells. In order to generate CD4+ T cell lines, intact ras p21 protein bearing the relevant amino acid substitution is used as the antigenic stimulus and autologous peripheral blood lymphocytes (PBL) or lymphoblastoid cell lines (LCL) immortalized by infection with Epstein Barr virus are used as antigen presenting cells. In order to generate CD8+ T cell lines, autologous antigen-presenting cells transfected with an expression vector which produces relevant mutated ras p21 protein are used as stimulator cells. Established T cell lines are cloned 2–4 days following antigen stimulation by plating stimulated T cells at a frequency of 0.5 cells per well in 96-well flat-bottom plates with $1 \times 10^6$ irradiated PBL or LCL cells and recombinant interleukin-2 (rIL2) (50 U/ml). Wells with established clonal growth are identified at approximately 2–3 weeks after initial plating and restimulated with appropriate antigen in the presence of autologous antigen-presenting cells, then subsequently expanded by the addition of low doses of rIL2 (10 U/ml) 2–3 days following antigen stimulation. T cell clones are maintained in 24-well plates by periodic restimulation with antigen and rIL2 approximately every two weeks.

Regardless of how an individual's T cells are proliferated in vitro, the T cells may be administered to the individual for therapeutic attack against a tumor. Thus, a patient's own T cells (autochthonous T cells) can be used as reagents to mediate specific tumor therapy. Typically, about $1 \times 10^9$ to $1 \times 10^{11}$ T cells/M$^2$ will be administered intravenously or intracavitary, e.g., in pleural or peritoneal cavities, or in the bed of a resected tumor. It will be evident to those skilled in the art that the number and frequency of administration will be dependent upon the response of the patient. Suitable carriers or diluents for T cells include physiological saline or sera. It will be recognized by one skilled in the art that the composition should be prepared in sterile form.

T cells may also be proliferated in vivo. For example, immunization of an individual with one or more protein expression products of activated oncogenes or cancer-related genes can induce continued expansion in the number of T cells necessary for therapeutic attack against a tumor. It may be desirable to administer the protein expression product repetitively.

The present invention also discloses that the protein expression products of activated oncogenes or cancer-related genes, in addition to being immunogenic to T cells, appear to stimulate B-cells to produce antibodies capable of recognizing these proteins. Detection of such antibodies provides another way to diagnose a malignancy in which an activated oncogene or cancer-related gene is associated with the malignancy. Antibodies specific (i.e., which exhibit a binding affinity of about $10^7$ liters/mole or better) for one or more protein expression products may be found in a variety of body fluids including sera and ascites. Detection of one or more immunocomplexes formed between a protein expression product and antibodies specific for the protein may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980–4983, 1980); enzyme-linked immunosorbent assays as described by, for example, Raines and Ross (*J. Biol. Chem.* 257:5154–5160, 1982); immunocytochemical techniques, including the use of fluorochromes (Brooks et al., *Clin. Exp. Immunol.* 39: 477, 1980); and neutralization of activity [Bowen-Pope et al., *Proc. Natl. Acad. Sci. USA* 81:2396–2400 (1984)], all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference.

For detection purposes, the protein expression products ("antigens") may either be labeled or unlabeled. When unlabeled, the antigens find use in agglutination assays. In addition, unlabeled antigens can be used in combination with labeled molecules that are reactive with immunocomplexes, or in combination with labeled antibodies (second antibodies) that are reactive with the antibody directed against the protein expression product, such as antibodies specific for immunoglobulin. Alternatively, the antigens can be directly labeled. Where they are labeled, the reporter group can include radioisotopes, fluorophores, enzymes, luminescers, or dye particles. These and other labels are well known in the art and are described, for example, in the following U.S. Pat. Nos.: 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1–5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

In one preferred embodiment of this aspect of the present invention, a reporter group is bound to the protein expression product. The step of detecting immunocomplexes involves removing substantially any unbound protein expression product and then detecting the presence or absence of the reporter group.

In another preferred embodiment, a reporter group is bound to a second antibody capable of binding to the antibodies specific for a protein expression product. The step of detecting immunocomplexes involves (a) removing substantially any unbound antibody, (b) adding the second antibody, (c) removing substantially any unbound second antibody and then (d) detecting the presence or absence of the reporter group. Where the antibody specific for the protein expression product is derived from a human, the second antibody is an anti-human antibody.

In a third preferred embodiment for detecting immunocomplexes, a reporter group is bound to a molecule capable of binding to the immunocomplexes. The step of detecting involves (a) adding the molecule, (b) removing substantially any unbound molecule, and then (c) detecting the presence or absence of the reporter group. An example of a molecule capable of binding to the immunocomplexes is protein A.

It will be evident to one skilled in the art that a variety of methods for detecting the immunocomplexes may be employed within the present invention. Reporter groups suitable for use in any of the methods include radioisotopes, fluorophores, enzymes, luminescers, and dye particles.

In a related aspect of the present invention, detection of immunocomplexes formed between a protein expression product of an activated oncogene, or cancer-related gene, and antibodies in body fluid which are specific for the protein may be used to monitor the effectiveness of cancer therapy. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

The following examples are offered by way of illustration and not by way of limitation.

Examples

EXAMPLE 1

Elicitation of Specific Class-II Restricted T-Cell Response to Mutated Ras Oncogene Products A. Immunization C57BL/6 and B6.C-H-$2^{bm12}$ mice (Jackson Laboratories, Bar Harbor, Me.) were inoculated with a synthetic peptide (Amino acid sequence: KLVVVGARGVGK; Microbiological Associates, Bethesda, Md.) which corresponds to residue 5–16 of the p21 protein product of mutated ras proto-oncogene encoding a residue 12 substitution of Arginine (R) for Glycine (G). The peptide was solubilized in distilled water at 1 mg/ml, emulsified in complete Freund's adjuvant (Sigma Co., St. Louis, Mo.) at a ration of 1:1, then injected subcutaneously into the base of the tail using a 25 gauge needle. Alternatively peptide was emulsified with Ribi MPL+TDM+CWS adjuvant (Ribi Immunochem. Res., Hamilton, Mont.) and injected subcutaneously into both hindquarters. Total amount of peptide injected was 50 μg per mouse. Seven days later animals were sacrificed and draining periaortic and inguinal lymph nodes were removed. Lymph nodes, suspended in buffered saline in petri dishes, were teased apart with 18 gauge needles. Dislodged lymphocytes were collected and washed with buffered saline then suspended at $1 \times 10^6$ cells per ml in culture medium for use in proliferation assays.

B. Proliferation Assay

Lymphocytes obtained from immunized mice were suspended in culture medium (consisting of RPMI 1640 Gibco supplemented with 10% fetal calf serum, 2 mM L-glutamine, 100 U/ml streptomycin, 100 U/ml penicillin and $2.5 \times 10^{-5}$ M 2-mercaptoethanol) and were plated in 96-well flat bottom microtiter plates (Costar Co., Cambridge, Mass.) at $1 \times 10^5$ cells per well. Syngeneic spleen cells which had been irradiated to 3000 rads were added at $2 \times 10^5$ cells per well to serve as antigen presenting cells. The immunizing peptide and indicated control peptides (50 μg/ml) were added to triplicate wells (final volume of 200 μl/well). The plates were incubated at 37° C. in humidified air containing 5% $CO_2$ for 72 hours then pulsed for 6 hr with 1 μCi per well of tritiated thymidine ($^3$H-TdR; 20 Ci/mmol from NEN Products, Boston, Mass.). Lymphocytes from individual wells were collected onto filter paper disks using a multi-channel harvester then transferred to scintillation fluid in individual counting tubes. β emission was measured using a Beckmann liquid scintillation spectrophotometer. The data presented in FIG. 1 represents the mean of triplicate determinations.

EXAMPLE 2

Generation of T Cell Lines and Clones With Specificity for the Protein Product of Mutated Ras Proto-Oncogene Lymphocytes obtained from draining lymph nodes of immunized mice as described above were plated ($4 \times 10^6$ cells per well) in 24-well culture plates (Costar Co.) with irradiated syngeneic spleen cells (10,000 rads; $2 \times 10^6$ cells per well) and immunizing peptide (5 μg/well) to give a final volume of 2 ml (culture medium). Plates were cultured for 5 days (37° C., 5% $Co_2$), then split 1:2 onto replicate plates. After ten days lymphocytes were restimulated by plating $5 \times 10^5$ cultured lymphocytes with $4 \times 10^6$ irradiated syngeneic spleen cells and peptide at 5 μg/ml. After three days, individual wells were redistributed into 2-4 wells of culture medium containing 10 units of Interleukin-2 (human recombinant from Hoffmann-LaRoche) to facilitate cell expansion. Lines were restimulated with antigen and subsequently IL-2 as described above, every 3-4 weeks.

Immune lymphocytes which had been twice stimulated with antigen in vitro were cloned at day 13 following initiation of culture (3 days following Ag restimulation) by plating immune T cells at a frequency of 0.5 cells per well in 96-well flat-bottom plates with irradiated syngeneic spleen cells ($1 \times 10^6$ cells per well) and Interleukin-2 at 50 U/ml. Wells with clonal growth were expanded and tested for immune specificity as shown in FIG. 2. Specific T cell clones were maintained as described for T cell lines.

EXAMPLE 3

T Cell Immunity to the Joining Region of p210$^{bcr-abl}$ Protein

A. Tumor Cell Lines, Peptides and Proteins

K562 is a Ph-chromosome-positive human CML cell line (Konopka & Witte, Cell 37:1035-1042, 1984). 8B1 and 106-5 are BALB/c murine leukemia cell lines derived by retroviral transformation of BALB/c bone marrow cells with p210 or p185 bcr-abl fusion genes, respectively (McLaughlin et al., Proc. Natl. Acad. Sci. USA 84:6558-6562, 1987; McLaughlin et al., Mol. and Cell. Biol. 9:1866-1674, 1989), and kindly provided by Dr. Owen Witte. K-BALB is a Kirsten murine sarcoma virus-transformed BALB/3T3 fibroblast tumor cell line. The amino acid sequences of synthetic peptides used (Table 1) were synthesized by M. Dojeski (FHCRC) using a peptide synthesizer (430A; Applied Biosystems, Foster City, Calif.) and purified by HPLC. To prepare bcr-abl protein extracts, K562, 8B1, 106-5 and K-BALB cells were harvested and resuspended in 25 mM potassium phosphate, pH 7.0, plus 2 mM EDTA, 100 mM NaCl, 1 mM PMSF, 50 μg/ml leupeptin, 100 units/ml aprotinin and 20 mM benzamidine (Pendergast et al., Mol. and Cell. Biol. 6:759-766, 1989). The cells were homogenized by use of ultrasonic cell disrupter Model W-380 (Heat Systems Ultrasonics, New York), centrifuged for 10 minutes at 3000 g and the supernates resedimented at 100,000 g for 90 minutes. The high molecular weight (>100,000 kD) supernatant proteins in the cell extracts were isolated and concentrated by using DIAFLO ultrafilter PM100 (Amicon, Mass.). The partially purified bcr-abl proteins were immunoprecipitated from the lysate with monoclonal antibody to bcr (Oncogene Science, New York), electrophoresed by SDS-PAGE and identified by Western immunoblotting with antibody to c-abl (Oncogene Science, New York). The bcr-abl proteins were aliquoted and stored at −70° C.

TABLE 1

Bcr-abl Peptide Amino Acid Sequences (joining point between positions 8 and 9 of bcr3-abl2 22 mer)

| Peptide | Length | Sequence |
|---|---|---|
| bcr3-abl2 | 22 mer* | I V H S A T G F K Q S S K A L Q R P V A S D |
| bcr3-abl2 | 18 mer | H S A T G F K Q S S K A L Q R P V A |
| bcr3-abl2 | 16 mer | G F K Q S S K A L Q R P V A S D |
| bcr3-abl2 | 14 mer | G F K Q S S K A L Q R P V A |
| bcr3-abl2 | 12 mer | G F K Q S S K A L Q R P |
| bcr3 | 12 mer | I V H S A T G F K Q S S |
| bcr2-abl2 | 12 mer | L T I N K E E A L Q R P |
| BCRI-abl2 | 14 mer | A F H G D A Q A L Q R P V A |

*Amino acids are represented by single letter code; bcr3-abl2 denotes sequences from the p210$^{bcr-abl}$ chimeric protein composed of bcr exon 3 fused to c-abl exon 2; bcr2-abl2 denotes sequences from the p210$^{bcr-abl}$ chimeric protein composed of bcr exon 2 fused to c-abl exon 2; BCRI-abl2 denotes sequences of p185$^{bcr-abl}$ chimeric protein composed of the BCRI region of the bcr gene fused to c-abl exon 2 (Gehly et al., Blood 78:458-465, 1991).

B. Immunization Protocols and Proliferative Assays

Mice (female BALB/c and C57BL/6 (B6), 6 to 8 weeks old; Jackson Laboratories, Bar Harbor, Me.) were inoculated twice at 2-week intervals by subcutaneous injection with Complete Freund's Adjuvant (Sigma Chemical Co., St. Louis, Mo.) alone or emulsified with bcr3-abl2 peptide (100 μg). Ten days after the final immunization, single cell suspensions of draining lymph nodes and spleens were prepared in medium consisting of 1:1 mixture of RPMI 1640 (Gibco Laboratories, Inc., Grand Island, N.Y.) and EHAA (Biofluids, Inc., Rockville, Md.) with $2.5 \times 10^{-5}$ M 2-ME, 200 U/ml penicillin, 200 U/ml streptomycin, 10 mM L-glutamine and 10% fetal calf serum. For proliferative assays, lymphocytes were cultured in 96-well plates at $2 \times 10^5$ cells per well with $4 \times 10^5$ irradiated syngeneic spleen cells (3,000 rad) and designated (total volume of 200 μl per well). Plates were incubated in a humidified atmosphere under 5% $CO_2$ tension at 37° C. for 72 hours, and then pulsed for 18 hours with 1 mCi of [$^3$H]-thymidine per well. Proliferative responses of cloned T cells utilized $2 \times 10^4$ cells per well with $5 \times 10^5$ irradiated syngeneic spleen cells (3,000 rad) and designated peptide.

C. Generation and Characterization of p210 bcr-abl-Specific T Cell Clones

Lymphocytes from the draining lymph nodes of mice immunized with bcr3-abl2 peptide were cultured in 24-well culture plates at $4 \times 10^6$ cells per well with $2 \times 10^6$ irradiated syngeneic spleen cells and bcr3-abl2 peptide at 25 μg/ml (total volume 2 ml). The plates were cultured in a humidified atmosphere under 5% $CO_2$ tension at 37° C. for 5 days then split 1:2. After 10 days, lymphocytes were restimulated at $1 \times 10^6$ lymphocytes per well in 24-well culture plates with $5 \times 10^6$ irradiated syngeneic spleen cells and peptide (25

μg/ml). Two days after the second in vitro stimulation, T cells were plated at 0.5 cells per well in 96-well flat-bottom plates with 1×10⁶ irradiated syngeneic spleen cells and rIL-2 (50 U/ml). Derived T cell clones were maintained by periodic stimulation with peptide (1 μg/ml) plus irradiated syngeneic spleen cells followed by expansion with rIL-2 (10 U/ml) every 2 weeks. T cell clones were stained with FITC-conjugated anti-Thy 1.2 (1%), or FITC-conjugated anti-Lyt2 (2%), or PE-conjugated anti-L3T4 (3%) mAbs (Becton Dickinson Immunocytochemistry Systems, Mountain View, Calif.) at 4° C. for 45 minutes.

D Synthetic Peptides Corresponding to the Joining Region of p210$^{bcr-abl}$ Protein Elicit T Cell Responses BALB/c mice were immunized with a synthetic 12 amino acid peptide identical to the joining region of the p210 protein in K562 CML cells, termed bcr3-abl2 peptide (Table 1). Immunity was validated by the demonstration that host lymph node and splenic lymphocytes from immunized mice proliferated in vitro in response to the immunizing peptide but not control peptides (FIG. 1). Similar data was generated in the B6 mouse strain. The immunizing peptide, G·F·K·Q·S·S·K·A·L·Q·R·P contained 6 amino acids from bcr (G·F·K·Q·S·S), 1 fusion amino acid (K) and 5 amino acids from c-abl (A·L·Q·A·P) (Table 1). To examine for fine specificity, the T cell lines were cloned by limiting dilution and maintained by episodic restimulation with the bcr3-abl2 peptide. All clones were Thy-1.2⁺ CD4⁺ CD8⁻ by analysis with fluoresceinated antibodies. Depending upon which bcr domains are included, the bcr-abl chimeric protein takes two major forms in CML (bcr2-abl2 and bcr3-abl2) and one major form in ALL (BCRI-abl2) (Canaani et al., in A. Deisseroth and R.B. Arlinghaus, eds., *Chronic Myelogenous Leukemia: Molecular Approaches to Research and Therapy*, Marcel Dekker, New York, Chap. 8, pp. 217–240, 1991; Gehly et al., *Blood* 78:458–465, 1991; Clark et al., *Science* 235:85–88, 1987; Kurzrock et al., *Nature* 325:631–635, 1987; Chan et al., *Nature* 325:635–637, 1987). In each case, the c-abl sequence of amino acids is identical but is joined with distinct bcr amino acid sequences. Data from 9 representative clones (Table 2) demonstrated that the immune T cells responded specifically to bcr3-abl2 but not to the alternate bcr-abl joining regions of bcr2-abl2 or BCRI-abl2. The immune T cells likewise failed to respond to peptides identical to the isolated amino acid sequence of bcr3 alone. Thus, the immunogenic determinant was specifically associated with the unique 12 amino acid residues of the joining region of the p210$^{bcr3-abl2}$ protein.

TABLE 2

Specificity of CD4⁺ T Cell Clones to a 12-Amino-Acid Peptide Corresponding to the Joining Region of the p210$^{bcr-abl}$ Chimeric Protein*

| T cell clones | [³H] Thymidine Incorporation (c.p.m.) | | | | | |
|---|---|---|---|---|---|---|
| | Media | bcr3-abl2 | bcr2-abl2 | BCRI-abl2 | bcr3 | Ras-c12 |
| 2E10 | 243 | 242,633 | 287 | 137 | 667 | 258 |
| 1D2 | 267 | 274,701 | 274 | 315 | 294 | 357 |
| 3B7 | 230 | 64,935 | 349 | 277 | 462 | 497 |
| 2E3 | 535 | 293,219 | 402 | 461 | 193 | 372 |
| 3E11 | 269 | 263,425 | 299 | 398 | 305 | 579 |
| 3G2 | 618 | 30,846 | 478 | 583 | 461 | 504 |
| 3G3 | 394 | 61,521 | 217 | 351 | 190 | 273 |
| 2B12 | 424 | 109,319 | 341 | 385 | 461 | 307 |

TABLE 2-continued

Specificity of CD4⁺ T Cell Clones to a 12-Amino-Acid Peptide Corresponding to the Joining Region of the p210$^{bcr-abl}$ Chimeric Protein*

| T cell clones | [³H] Thymidine Incorporation (c.p.m.) | | | | | |
|---|---|---|---|---|---|---|
| | Media | bcr3-abl2 | bcr2-abl2 | BCRI-abl2 | bcr3 | Ras-c12 |
| 2D4 | 532 | 262,799 | 143 | 147 | 133 | 259 |

*Resting CD4⁺ T cell clones of BABL/c origin were cultured with irradiated syngeneic spleen cells as APC plus the indicated peptides at 5 μg/ml.
The data represent the mean of triplicate determinations of [³H] thymidine incorporated for the final 18 hours of a 96-hour culture. The standard deviations were <10% of the c.p.m.

The concentration of bcr3-abl2 peptide necessary to induce proliferation varied. In general, optimal stimulation occurred in the range of 1 to 5 μg/ml, but some clones responded vigorously to as low as 0.04 μg/ml, the lowest concentration tested (Table 3).

TABLE 3

Proliferative Response of CD4⁺ T Cell Clones to Varying Concentrations of a 12-Amino-Acid Peptide Corresponding to the Joining Region of the p210$^{bcr-abl}$ Chimeric Protein*

| Responding T cell clones | [³H] Thymidine Incorporation (c.p.m.) after Stimulation with bcr3-abl2 12 mer peptide (μg/ml) | | | | | |
|---|---|---|---|---|---|---|
| | Media | 25 | 5 | 1 | 0.2 | 0.04 |
| 2E10 | 471 | 131,643 | 312,783 | 333,056 | 235,103 | 26,195 |
| 1D2 | 496 | 66,329 | 259,018 | 183,229 | 91,251 | 16,423 |
| 3B7 | 421 | 53,441 | 149,640 | 111,212 | 56,967 | 60,957 |
| 2E3 | 399 | 358,253 | 407,729 | 273,273 | 93,921 | 1,475 |
| 3E11 | 556 | 40,755 | 130,633 | 189,843 | 135,985 | 91,240 |
| 3G2 | 561 | 132,024 | 168,387 | 150,799 | 49,602 | 9,440 |
| 3G3 | 455 | 101,280 | 143,670 | 93,219 | 18,403 | 11,510 |
| 2B12 | 364 | 132,620 | 229,010 | 213,089 | 71,651 | 4,132 |
| 2D4 | 387 | 42,623 | 182,266 | 256,606 | 150,711 | 12,599 |

*Resting T cell clones were cultured with irradiated syngeneic spleen cells as APC plus bcr3-abl2 12 mer peptide at the indicated concentration.
The data represent the mean of triplicate determinations of [³H] thymidine incorporated for the final 18 hours of a 96-hour culture. The standard deviations were <10% of the c.p.m.

Antigen-specific responses of CD4⁺ T cells require not only binding to class II MHC molecules on APC but also display of the antigenic epitope in the proper orientation in the MHC cleft. Two bcr3-abl2-specific T cell clones derived by immunization with a 12 mer bcr3-abl2 peptide were tested for response to 14-, 16-, 18-, and 22-mer peptides synthesized to be identical to the naturally occurring amino acid sequences of the p210 joining region. The 12 mer bcr3-abl2 peptide-specific T cells responded to each of the longer peptides (Table 4), implying that a broad spectrum of joining region peptides could be appropriately presented by class II MHC molecules.

TABLE 4

Proliferative Response of CD4⁺ T Cell Clones to Bcr3-abl2 Peptides of Varying Lengths*

| Responding T cell clones | [³H] Thymidine Incorporation (c.p.m.) after Stimulation with bcr3-abl2 peptide (5 μg/ml) | | | | |
|---|---|---|---|---|---|
| | Media | 12-mer | 14-mer | 16-mer | 18-mer | 22-mer |
| 2E10 | 589 | 96,525 | 170,085 | 139,083 | 224,674 | 29,509 |
| 1D2 | 159 | 120,049 | 238,297 | 108,309 | 150,309 | 21,208 |

*Resting T cell clones were cultured with irradiated syngeneic spleen cells as APC plus bcr3-abl2 peptides of the above-varied lengths (see Table 1 for structure of peptides).
The data represent the mean of triplicate determinations of [³H] thymidine incorporated for the final 18 hours of a 96 hour culture. The standard deviations were <10% of the c.p.m.

E. Bcr3-abl2 Peptide-Specific T Cells Recognize p210 bcr-abl Protein

Partially purified p210$^{bcr-abl}$ protein from K562 and 8B1 tumor cells, p185$^{bcr-abl}$ protein from 106-5 tumor cells, and irrelevant proteins from K-BALB tumor cells were prepared. Several bcr3-abl2 peptide-specific CD4+ T cell clones were tested in a proliferative assay with irradiated synergenic APC plus either bcr2-abl2 peptide or partially purified bcr-abl proteins. Bcr2-abl2 peptide-specific T cells responded to p210$^{bcr-abl}$ protein, but not to p185$^{bcr-abl}$ protein or irrelevant K-BALB proteins (Table 5). The proliferative response to p210$^{bcr-abl}$ protein was less than the response to peptide, presumably due to either less joining region segments being present in the protein preparation on a per weight basis or to competition for binding to MHC molecules by alternative segments of the protein.

TABLE 5

Proliferative Response of bcr3-abl2 peptide-specific T Cell Clone to p210$^{bcr-abl}$ Chimeric Proteins*

| Peptide and Proteins | [$^3$H] Thymidine Incorporation (c.p.m.) after Stimulation with bcr-abl 12 peptide/proteins (μg/ml) | | | |
|---|---|---|---|---|
| | Media | 1 | 0.2 | 0.04 |
| bcr3-abl2 14-mer peptide | 214 | 92,970 | 54,896 | 6,303 |
| p210$^{bcr-abl}$ from K562 | 207 | 6,679 | 2,270 | 338 |
| p210$^{bcr-abl}$ from 8B1 | 521 | 2,498 | 1,483 | 236 |
| p185$^{bcr-abl}$ from 106-5 | 231 | 157 | 198 | 312 |
| Proteins from K-BALB | 164 | 197 | 276 | 284 |

*Bcr3-abl2 peptide-specific CD4+ T cell clone 2E10 (see Table 2 for specificity) was cultured with irradiated syngeneic spleen cells as APC plus the indicated concentration of bcr3-abl2 14-mer peptide or with partially purified protein isolated from K562 and 8B1 containing p210$^{bcr-abl}$; or from 106-5 containing p185$^{bcr-abl}$; or from irrelevant K-BALB tumor cells.

The data represent the mean of triplicate determinations of [$^3$H] thymidine incorporated for the final 18 hours of a 96-hour culture. The standard deviations were <10% of the c.p.m.

EXAMPLE 4

Figure 7:
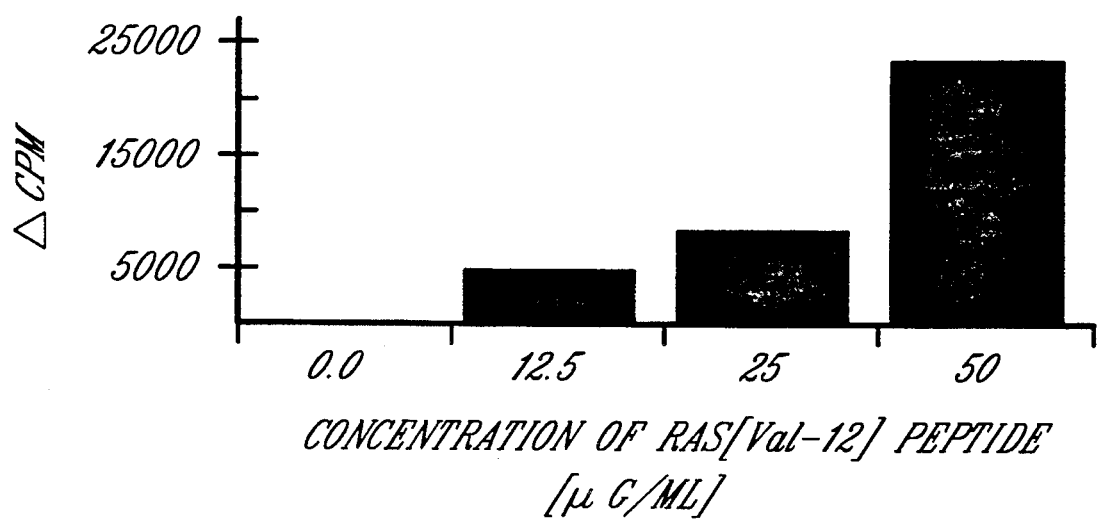
FIG. 7 graphically illustrates that spleen cells sensitized with FBL ras [Val-12] tumor cells in vivo respond specifically to ras [Val-12] peptide in vitro. C57BL/6 mice were immunized with irradiated FBL tumor cells (a Friend virus induced leukemia cell line) that had been transfected with the ras [Val-12] oncogene. Mice were injected twice with $5 \times 10^6$ irradiated tumor cells at an interval of two weeks. Approximately four weeks after the second inoculation, spleen cells were harvested and tested for the ability to respond to p5-17 ras [Val-12] peptide at the indicated concentrations. Spleen cells from mice immunized with FBL tumor that had been transfected with a normal ras [Gly-12] proto-oncogene evidenced no increased proliferative response to the same concentrations of the ras [Val-12] peptide.

Tumors Expressing Aberrant ras Protein in vivo Elicit T Cells Specific for Corresponding ras Peptide The following experiments show that aberrant ras p21 protein produced by tumor cells in vivo elicits T cells which proliferate specifically in response to the altered region of the ras p21 protein. A Friend virus induced leukemia cell line, designated as FBL, was transfected with the T24 Ha-ras-1 oncogene carried by the pH06T1 plasmid under control of a Moloney virus LTR and an SV40 enhancer to enable eukaryotic expression (Spandidos and Wilkie, *Nature* 310:469–475, 1984). The T24 oncogene encodes aberrant ras p21 protein with valine substituted for the normal glycine at residue-12 (Reddy et al., *Nature* 300:149–152, 1982). Expression of ras p21 [Val-12] by the transfected FBL cells was confirmed by western analysis using a monoclonal antibody which specifically binds to ras p21 [Val-12] proteins. Syngeneic B6 mice were immunized twice at two-week intervals with FBL cells transfected with the pH06T1 plasmid or a corresponding plasmid pH06NI which carries the normal Ha-ras-1 gene. Spleen cells from mice immunized with FBL transfected with the T24 oncogene proliferated in response to the ras [Val-12] peptide (FIG. 7), whereas spleen cells from mice immunized with FBL transfected with normal Ha-ras-1 did not respond.

EXAMPLE 5

CD4+ Ras-Specific T Cells can Mediate Tumor Therapy in vivo

Figure 8:
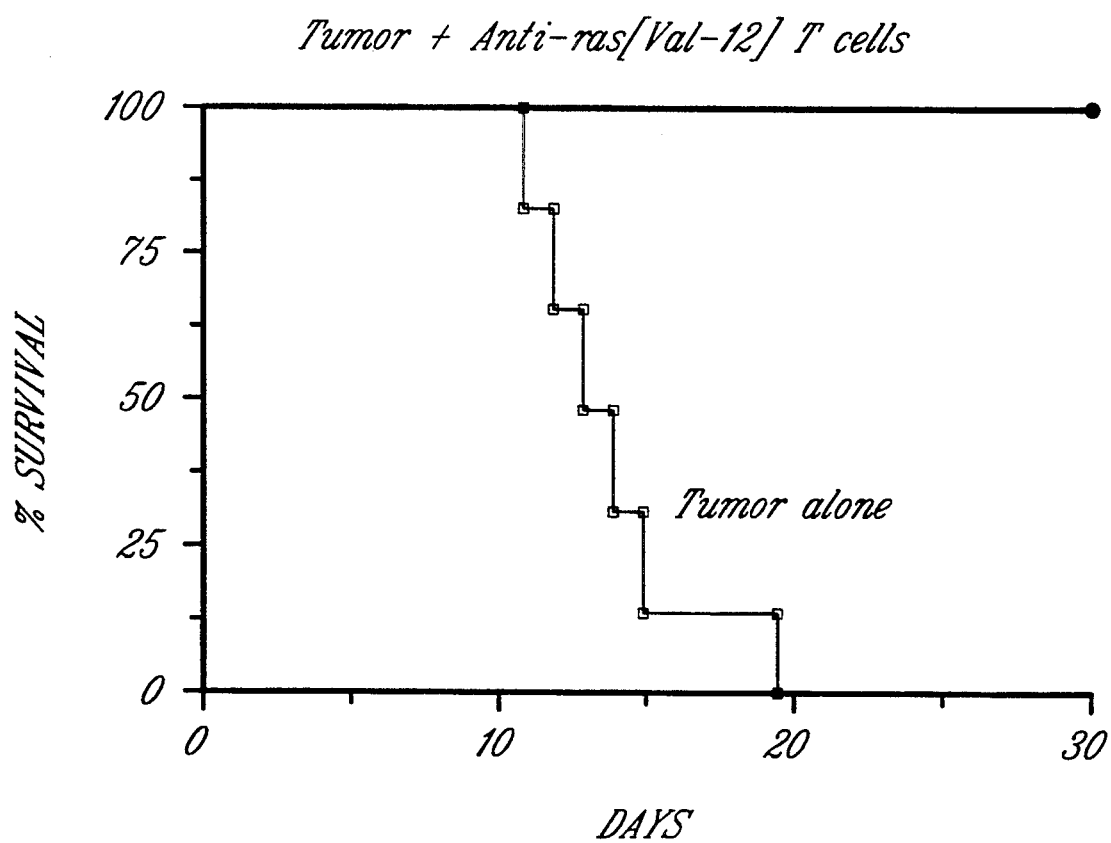
FIG. 8 graphically illustrates that T cells specific for ras p21 [Val-12] protein protect mice from challenge with a tumor that expresses the corresponding p21$^{ras}$ protein. BALB/c x B6 F1 mice (6 per group) were injected i.p. with RAS4 tumor cells ($3 \times 10^5$ cells per mouse) alone or in conjunction with B6 anti-p5-17 ras [Val-12] T cells ($2 \times 10^7$ cells per mouse). RAS4 is a tumorigenic line that was derived by transfection of the NIH3T3 cell line with the T24 oncogene encoding ras p21 [Val-12] protein. The anti-ras [Val-12] T cell line was generated by in vivo priming of B6 mice and subsequent periodic in vitro stimulation of spleen cells with the p5-17 [Val-12] ras peptide. The T cell line proliferates specifically to the sensitizing peptide and to intact ras p21 [Val-12] protein.

The finding (Example 4) that tumors which express aberrant ras p21 in vivo can elicit ras-specific T cells in vivo strongly implies that ras p21 is available to APC for processing and presentation to class II-restricted T cells in vivo. Presentation of the activated ras p21 in proximity to tumor cells may elicit class II-restricted T cells which can mediate substantial therapeutic effects in vivo against tumors even if the latter do not express class II MHC molecules and cannot be directly recognized. The ras 4 tumor, which expresses a transfected T24 oncogene and is tumorigenic in BALB/c×C57BL/6 F1 mice, was used in therapy. Small doses of tumor cells (3×10$^6$), injected i.p., kill animals within 2 weeks. A T cell line specific for the altered region of ras p21 [Val-12] was tested for the ability to protect BALB/c×C57BL/6 F1 mice against challenge with ras 4 tumor cells (3×10$^6$ i.p.) In repeated experiments, mice injected with tumor alone all died by day 19, whereas mice injected concurrently with tumor cells plus ras [Val-12] specific T cells (2×10$^7$ cells i.p.) all survived without evidence of tumor for greater than 8 weeks of observation (FIG. 8).

A second tumor therapy model was established with K-BALB tumor cells which express ras p21 [Ser-12] and syngeneic T cells which specifically recognize a corresponding synthetic ras [Ser-12] peptide. BALB/c mice injected with tumor cells (2×10$^5$) received either no additional therapy, or ras [Ser-12] specific T cells (1×10$^7$ cells per mouse) plus low doses of exogenous rIL-2 (5,000 U i.p. per day on days 0–4). Mice treated with ras specific T cells evidenced substantial extension of median survival. In related experiments, cohorts of BALB/c mice were sensitized with the ras [Ser-12] peptide or with adjuvant alone then challenged with a lethal dose of K-BALB tumor cells. Mice sensitized with ras peptide survived longer than non-immunized mice. Therefore, ras-specific class II-restricted T cells can mediate anti-tumor efficacy in vivo.

From the foregoing, it will be evident that, although specific embodiments of the invention have been described herein for purposes of illustration, various modifications may be made without deviating from the spirit and scope of the invention.

We claim:

1. A method for the detection of a malignancy in a warm-blooded animal, wherein an activated oncogene or cancer-related gene is associated with the malignancy, wherein said activated oncogene is ras or bcr-abl, comprising the steps of:
   (a) isolating T cells from the warm-blooded animal;
   (b) incubating the T cells with at least one protein expression product of an activated oncogene associated with the malignancy, wherein said activated oncogene is ras or bcr-abl; and
   (c) detecting the presence or absence of proliferation of the T cells, thereby determining the presence or absence of the malignancy.

2. The method of claim 1 wherein the step of detecting comprises measuring the rate of DNA synthesis of the T cells.

* * * * *

UNITED STATES PATENT AND TRADEMARK OFFICE
CERTIFICATE OF CORRECTION

PATENT NO. : 5,320,947
DATED : June 14, 1994
INVENTOR(S) : Martin A. Cheever and David J. Peace It is certified that error appears in the above-identified patent and that said Letters Patent is hereby corrected as shown below:

In column 18, claim 1, line 51, please delete "or cancer-related gene".

Signed and Sealed this

Eleventh Day of October, 1994

Attest:

BRUCE LEHMAN

Attesting Officer  Commissioner of Patents and Trademarks